United States Patent
Hunt et al.

(10) Patent No.: US 8,267,904 B2
(45) Date of Patent: Sep. 18, 2012

(54) MEDICINAL DELIVERY DEVICE

(75) Inventors: Ronald Douglas Hunt, Waxhaw, NC (US); Paul Bradley Forrest, Cary, NC (US)

(73) Assignee: The Hunt Project, LLC, Waxhaw, NC (US)

( * ) Notice: Subject to any disclaimer, the term of this patent is extended or adjusted under 35 U.S.C. 154(b) by 139 days.

(21) Appl. No.: 12/939,224

(22) Filed: Nov. 4, 2010

(65) Prior Publication Data

US 2012/0116325 A1 May 10, 2012

(51) Int. Cl.
*A61M 31/00* (2006.01)

(52) U.S. Cl. .................. 604/285; 604/275; 128/204.12

(58) Field of Classification Search .................. 604/275, 604/285; 128/204.12, 206.11
See application file for complete search history.

(56) References Cited

U.S. PATENT DOCUMENTS

| | | | |
|---|---|---|---|
| 2,243,360 A | 5/1941 | Slatis | |
| 2,620,795 A | 12/1952 | Muhlethaler | |
| 2,777,442 A | 1/1957 | Zelaib et al. | |
| 3,788,296 A | 1/1974 | Klatt et al. | |
| 4,030,491 A | 6/1977 | Mattila | |
| RE35,408 E | 12/1996 | Petruson | |
| 5,850,834 A | 12/1998 | Yoshida et al. | |
| 5,922,006 A | 7/1999 | Sugerman | |
| 6,386,197 B1 * | 5/2002 | Miller | 128/206.11 |
| 7,108,198 B2 | 9/2006 | Altadonna, Jr. | |
| 7,837,649 B1 | 11/2010 | Aboff | |
| 2002/0153007 A1 | 10/2002 | Davi | |
| 2004/0079814 A1 * | 4/2004 | Altadonna, Jr. | 239/34 |
| 2005/0257793 A1 | 11/2005 | Tatsumoto | |

FOREIGN PATENT DOCUMENTS

| | | |
|---|---|---|
| JP | 2002306598 A | 10/2002 |
| WO | 2009027876 A1 | 3/2009 |

OTHER PUBLICATIONS http://www.skymall.com/shopping/detail.htm?pid=101906204&c, Breathe Fit Snoring Aid, last accesses Nov. 12, 2010.
U.S. Appl. No. 29/378,400, filed Nov. 4, 2010.
Combined Search and Examination Report by United Kingdom Intellectual Property Office dated Feb. 13, 2012.
http://www.morningsicknesssoothers.com/products-page, website, last accessed May 23, 2011.
Examination report dated May 3, 2012 for related GB application GB1119006.3.

* cited by examiner

*Primary Examiner* — Kevin C Sirmons
*Assistant Examiner* — Emily Schmidt
(74) *Attorney, Agent, or Firm* — Olive Law Group, PLLC (57) ABSTRACT

A medicinal delivery device is provided. The device includes a clip defining an ala inner surface-engaging portion about a first end thereof. The clip also defines an ala outer surface-engaging portion about a second end thereof. The ala outer surface-engaging portion is in spaced-apart and generally inward facing arrangement relative to the first end of the clip. This forms a gap between the ala inner surface-engaging portion and the ala outer surface-engaging portion for receiving a patient's ala. A medicine chamber is carried about the first end of the clip for dispensing medicine into the patient's nasal cavity.

15 Claims, 6 Drawing Sheets

FIG. 8 ously, there remains a need for an aromatherapy medicinal delivery device that addresses the various disadvantages associated with conventional devices.

MEDICINAL DELIVERY DEVICE

TECHNICAL FIELD

The presently disclosed subject matter is directed towards a medicinal delivery device, and more particularly towards a medicinal delivery device for delivering aromatic treatment to the olfactory receptors in the nose of a patient.

BACKGROUND

Aromatherapy is a scientific art of using oils for the treatment of illness or restoring health, beauty, and well being. Aromatherapy may be accomplished in many different ways, and one effective way is the insertion of an aroma containing member into the nasal cavity of a patient.

Various devices have been designed to deliver aromatherapy in this manner, however, these devices have had various disadvantages associated therewith. For example, some devices have featured a clip that engaged the septum of the patient and had sponges on each end of the clip that contained aromatic oils or other medicines. This design was undesirable because direct contact could occur between the patient and the aromatic oils, causing burns to the patient's skin. Still other designs utilized small containers on the ends of the clip that would contain aromatic oils or other medicines. This design was undesirable because oils could spill from the small containers and cause burns or irritation to the patient's skin.

Accordingly, there remains a need for an aromatherapy medicinal delivery device that addresses the various disadvantages associated with conventional devices.

SUMMARY

According to one aspect of the disclosed subject matter, a medicinal delivery device is provided. The device includes a clip that defines an ala inner surface-engaging portion about a first end thereof and an ala outer surface-engaging portion about a second end thereof. The ala outer surface-engaging portion is in spaced-apart and general inwardly facing arrangement relative to the first end to thereby define a gap therebetween for receiving a patient's ala. A medicine is carried about the first end of the clip for dispensing medicine into the patient's nasal cavity.

According to one aspect of the disclosed subject matter, the clip generally approximates a U-shape.

According to one aspect of the disclosed subject matter, the clip defines an outwardly extending arcuate flange on the first end thereof for providing a surface for removal of the clip.

According to one aspect of the disclosed subject matter, the medicine is carried within a cavity that is defined in a housing on the first end of the clip.

According to one aspect of the disclosed subject matter, the device includes a cover for engaging the cavity and enclosing the medicine therein.

According to one aspect of the disclosed subject matter, the cover defines a tab and the housing defines a slot for receiving the tab and selectively engaging the cover thereto.

According to one aspect of the disclosed subject matter, the device includes a resilient pad on the ala inner surface-engaging portion that extends so as to cover the slot. The pad provides comfort to the patient's skin and prevents flow-through of medicine through the slot.

According to one aspect of the disclosed subject matter, the cover defines at least one vent for allowing flow-through of medicine into the patient's nasal cavity.

According to one aspect of the disclosed subject matter, the device includes a selectively removable seal that extends across the cover and a surface of the housing for sealing the medicine therein.

According to one aspect of the disclosed subject matter, the medicine is carried by an absorbent material.

According to one aspect of the disclosed subject matter, a medicinal delivery device is provided. The device includes a generally arcuate clip having first and second ends. The first end defines an ala inner surface-engaging portion and the second end defines an ala outer surface-engaging portion that is in spaced-apart and mutually facing arrangement relative to the ala inner surface-engaging portion. This arrangement forms a gap for receiving a patient's ala. A medicine chamber is carried about the first end and defines a cavity within a housing for containing a medicine. A cover is in selective engagement with the housing for enclosing the medicine and further defines at least one vent for allowing flow-through of medicine into the patient's nasal cavity.

According to one aspect of the disclosed subject matter, a medicinal delivery device is provided. The device includes a clip that defines an ala inner surface-engaging portion about a first end thereof and an ala outer surface-engaging portion about a second end thereof. The first and second ends are in generally laterally spaced-apart relation and define a gap therebetween for receiving a patient's ala. A medicine chamber is carried about the first end and defines a cavity within a housing for containing an absorbent medicine material. A cover is configured for cooperative engagement with the housing and defines at least one vent through a surface thereof for allowing flow-through of medicine into the patient's nasal cavity.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Further, the claimed subject matter is not limited to implementations that solve any or all disadvantages noted in any part of this disclosure.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed subject matter is not limited to the specific methods and instrumentalities disclosed. In the drawings.

DETAILED DESCRIPTION

The presently disclosed subject matter now will be described more fully hereinafter with reference to the accompanying drawings, in which some, but not all embodiments are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
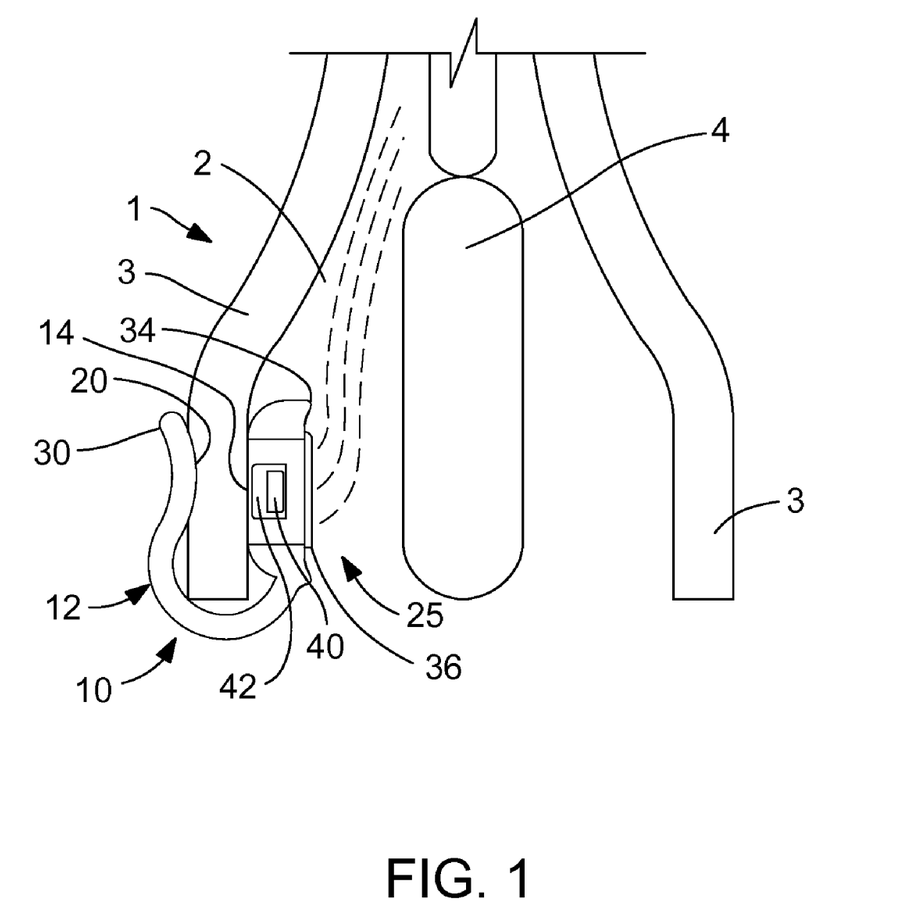
FIG. 1 is a front cross-sectional view of a nasal cavity of a patient having a medicinal delivery device installed therein according to one embodiment of the presently disclosed subject matter.

FIG. 1 illustrates a cross-sectional view of a patient's nose 1 having a medicinal delivery device installed therein that is generally designated as 10 throughout the drawings. The device 10 is operable for delivering any medicinal fluid, including aromatic fluids if desired. As used herein, medicinal fluid may include any solid, liquid, or gaseous medicine. The device 10 includes a clip that is generally designated 12. The device 10 is configured for being installed about the patient's nose 1 within their nasal cavity 2. The nose 1 defines the nasal cavity 2, which is formed between the patient's ala 3 and septum 4. The device is configured for being received by the patient's ala 3 and being sized such that a medically suitable distance is maintained between the device 10 and the patient's septum 4.

With additional reference to FIGS. 2A, 2B, 3A, 3B, 4A, 4B, 5A, 5B, 6A, and 6B, the clip 12 defines an ala inner surface-engaging portion 14 about a first end 16 of the clip 12. The engagement of the ala inner surface-engaging portion 14 and the inner ala surface is depicted in FIG. 1. The clip 12 further defines an ala outer surface-engaging portion 20 about a second end thereof. The ala outer surface-engaging portion 20 is in spaced-apart and generally facing arrangement relative to the first end 16. In this manner, a gap 24 is formed between the ala inner surface-engaging portion 14 and the ala outer surface-engaging portion 20 for receiving the patient's ala 3. As used herein, ala outer surface shall mean the ala surface outside of the nasal cavity 2, while ala inner surface shall mean the ala surface inside of the nasal cavity 2.

Figure 2A:
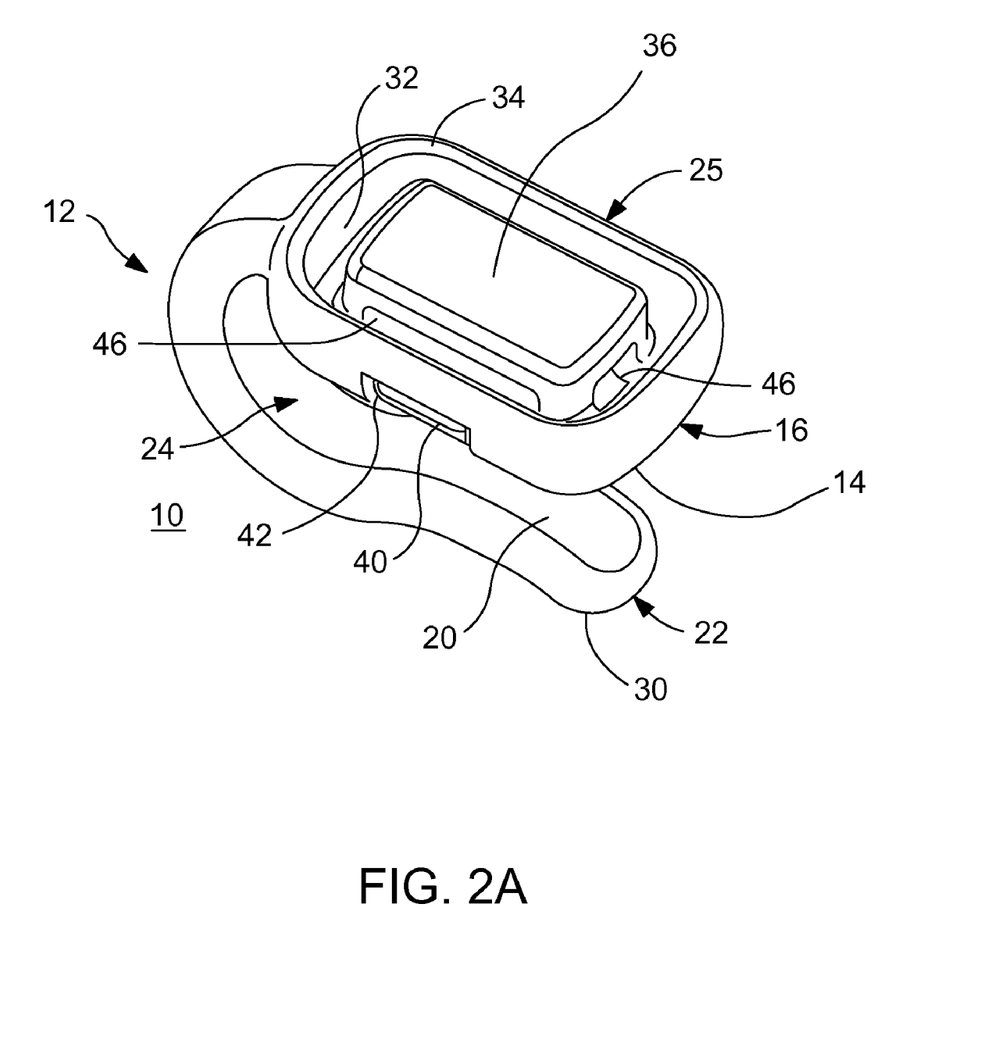
FIG. 2A is a perspective view of the medicinal delivery device according to one embodiment of the presently disclosed subject matter.
Figure 2B:
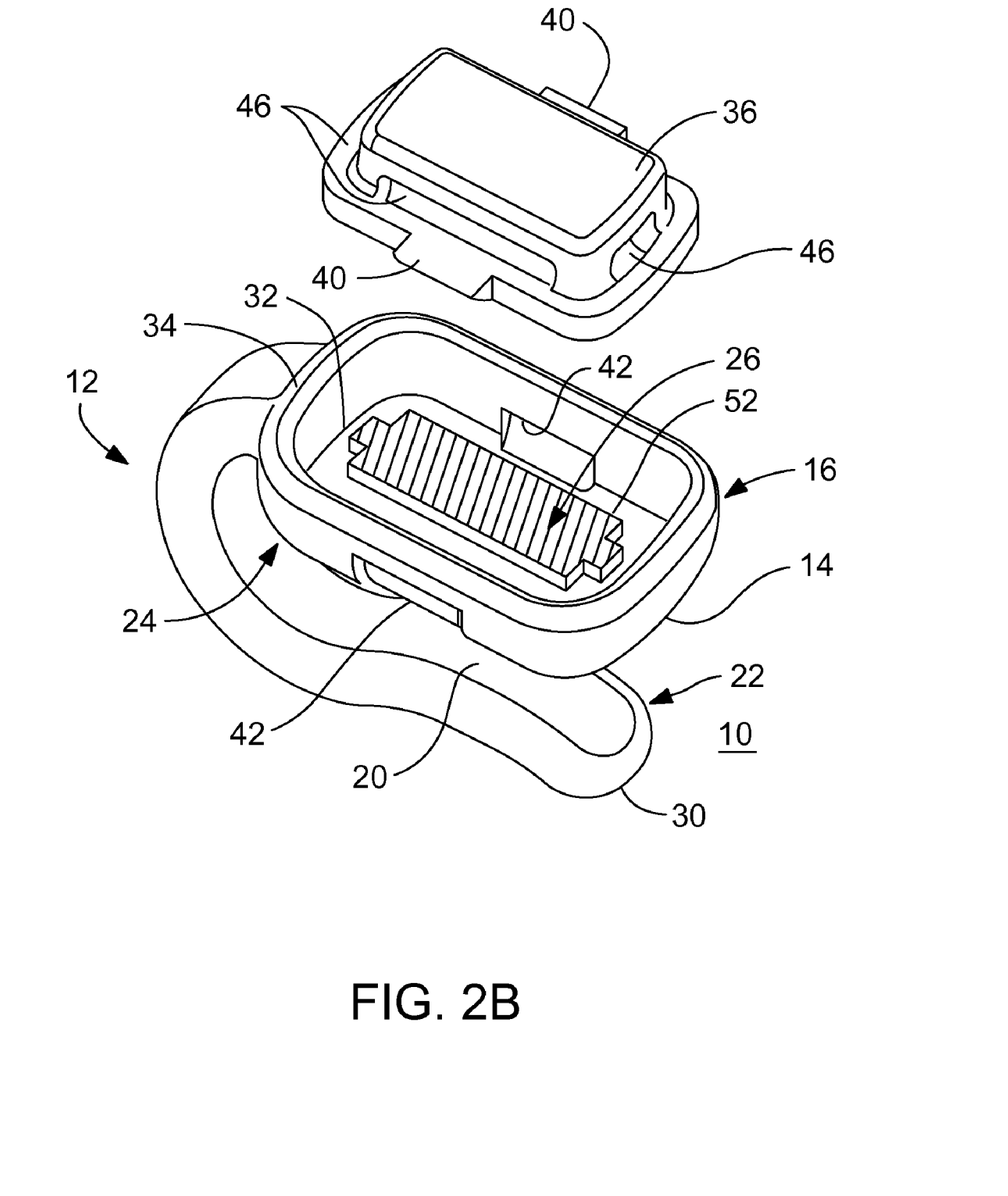
FIG. 2B is an exploded perspective view of the medicinal delivery device illustrated in FIG. 2A according to one embodiment of the presently disclosed subject matter.
Figure 3A:
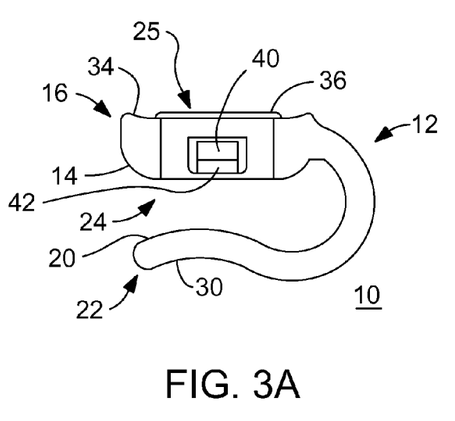
FIG. 3A is a side view of the medicinal delivery device according to one embodiment of the presently disclosed subject matter.
Figure 3B:
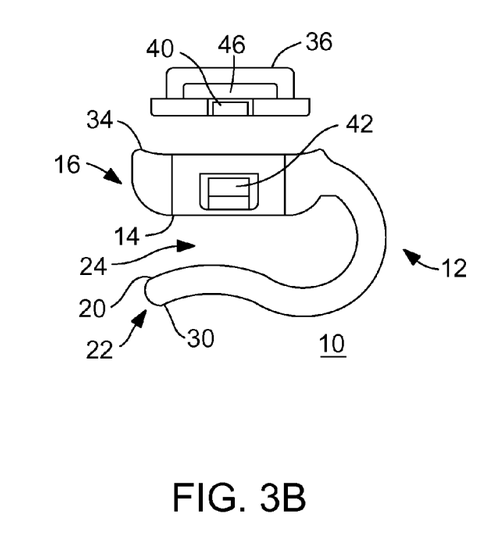
FIG. 3B is an exploded side view of the medicinal delivery device illustrated in FIG. 3A according to one embodiment of the presently disclosed subject matter.
Figure 4A:
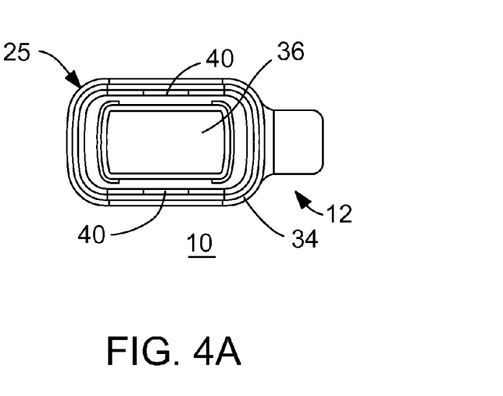
FIG. 4A is a top view of the medicinal delivery device according to one embodiment of the presently disclosed subject matter.
Figure 4B:
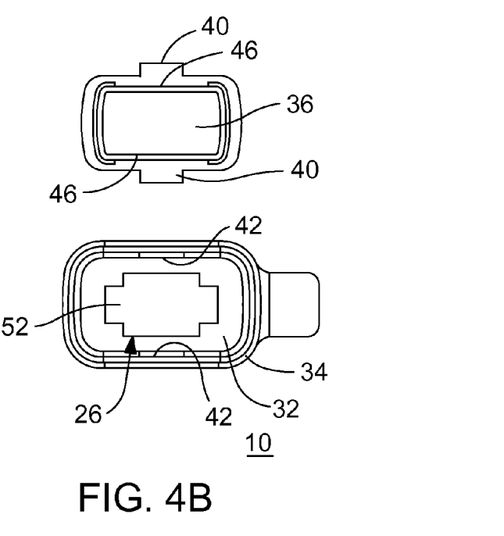
FIG. 4B is an exploded top view of the medicinal delivery device illustrated in FIG. 4A according to one embodiment of the presently disclosed subject matter.

A medicine chamber is generally defined as 25 and is carried about the first end 16 of the clip 12. The medicine chamber 25 is provided for storing medicine and allowing dispensing of that medicine into the patient's nasal cavity 2 via fluid flow depicted as broken lines in FIG. 1 that includes a mixture of air and aroma wafting from the medicine chamber 25. As illustrated in FIG. 2B, a medicine 26 may be carried within a cavity 32 that is defined in a housing 34 formed about the first end 16 of the clip 12. The medicine chamber 25 may have a greater width than the remaining portions of the clip 12. In this manner, the medicine chamber 25 has a sufficient size to contain a sufficient amount of medicine, but the portions of the clip 12 that would be exposed and viewable outside of the patient's nasal cavity are relatively small.

The device 10 may further include a cover 36 for engaging the cavity 32 and enclosing the medicine 26 therein. The cover 36 may be transparent or opaque and in one or more embodiments may be selectively engageable with the device 10. The cover 36 may define a tab 40 that is configured for being selectively received and engaged with a corresponding slot 42 that is defined in the housing 34. In this manner, the cover 36 may have sufficient resiliency to be bent along a longitudinal axis such that the distance between opposing tabs 40 decreases until the tabs 40 may be received by the corresponding slots 42. The cover 36 is then released and returns to its original dimensions and is then engageably secured within housing 34 by receiving engagement of the tabs 40 in the slots 42.

Figure 5A:
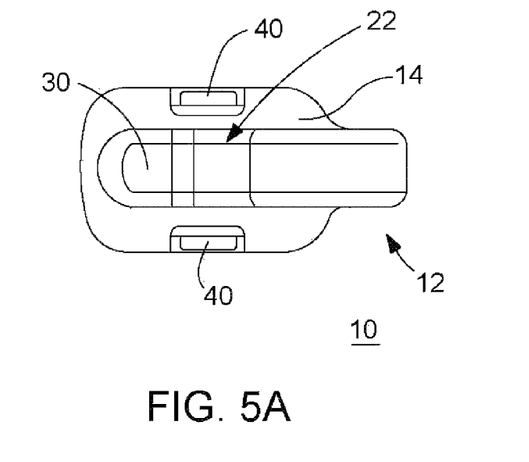
FIG. 5A is a bottom view of the medicinal delivery device according to one embodiment of the presently disclosed subject matter.
Figure 5B:
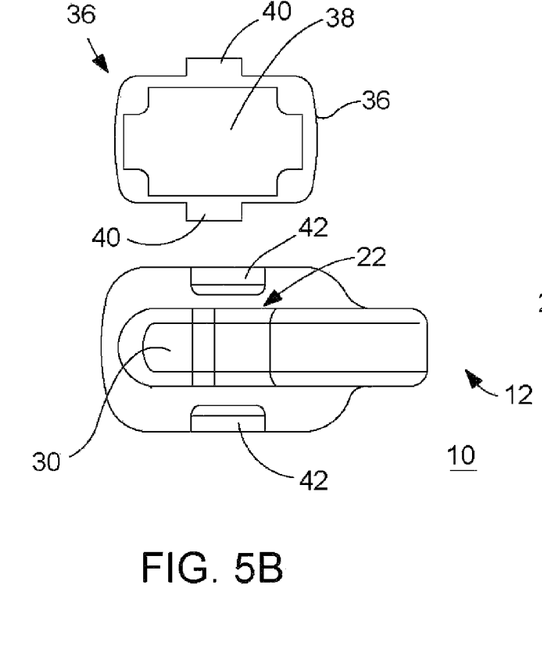
FIG. 5B is an exploded bottom view of the medicinal delivery device illustrated in FIG. 5A according to one embodiment of the presently disclosed subject matter.
Figure 6A:
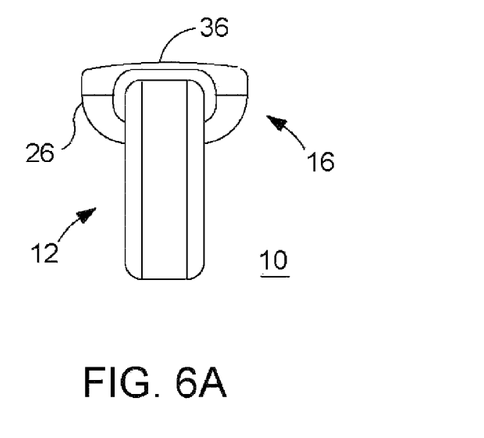
FIG. 6A is a rear view of the medicinal delivery device according to one embodiment of the presently disclosed subject matter.
Figure 6B:
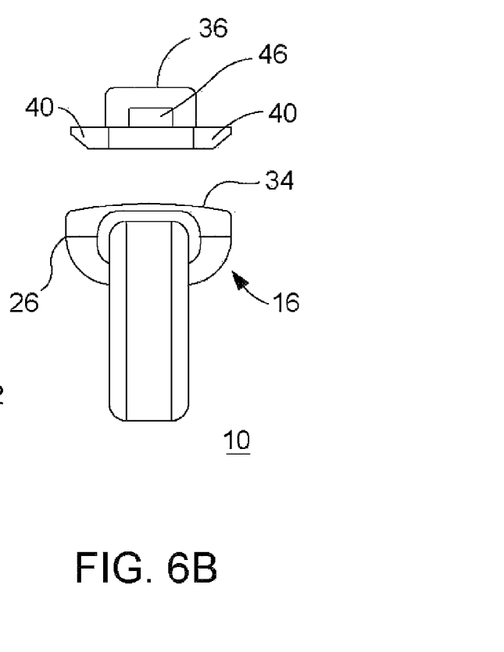
FIG. 6B is an exploded rear view of the medicinal delivery device illustrated in FIG. 6A according to one embodiment of the presently disclosed subject matter.
Figure 7:
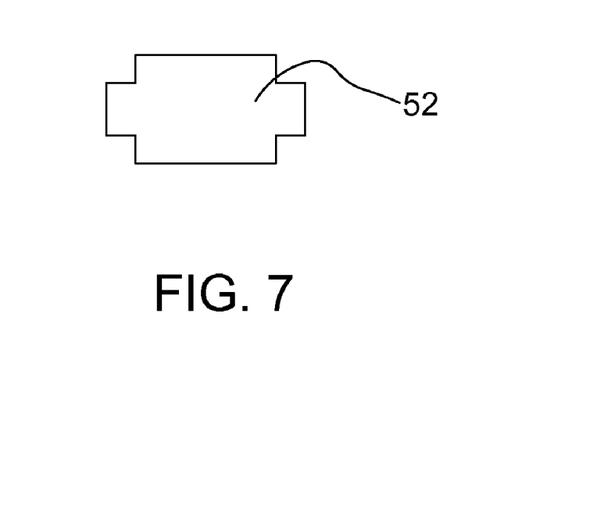
FIG. 7 is a perspective view of an absorbent material for absorbing medicine for use with a medicinal delivery device according to one embodiment of the presently disclosed subject matter.

With reference to FIGS. 2B, 5B, and 7, the medicine 26 may be carried in an absorbent material 52 that may be sized and configured for being received in the housing 34 in cooperation with a volume 38 defined in the underside of the cover 36. The absorbent material 52 may be secured to one of the housing 34 or cover 36, or may be carried by compressive engagement of the cover 36 when installed in the housing 34 or any other suitable manner. In one or more embodiments, the absorbent material 52 may have a cross-sectional dimension that approximates a corresponding cross-sectional dimension of the volume 38 so as to maximize the total volume of the absorbent material 52. In one or more embodiments, the absorbent material 52 may be configured for absorbing one tenth of a cubic centimeter of medicine, while in other embodiments, the absorbent material 52 may absorb differing amounts of medicine. The absorbent material 52 may be a sponge-like material, open or closed-cell foam, or any appropriate material. Additionally, in one or more embodiments, an absorbent material 52 may not be employed, and, as a non-limiting example, solid medicines configured for releasing an aroma may be utilized and placed within the medicine chamber 25.

The cover 36 may define a vent 46 for allowing flow-through of medicine from the volume 38 into the patient's nasal cavity 2. In one or more embodiments, multiple vents 46 may be provided as illustrated throughout the Figures. The vents 46 are configured for facing away from the inner ala surface and instead face into the patient's nasal cavity 2, thereby reducing the risk of inadvertent direct exposure to the medicine. In alternate embodiments, cover 36 may be formed from a porous or semi-porous material that allows flow-through of medicine into the patient's nasal cavity 2. Additionally, the vents 46 may serve as a fill port for allowing injection of medicine into the absorbent material 52. In this manner, the device 10 may be provided in a retail or wholesale setting without an aromatic medicine contained therein, and alternatively, a health care provider or patient may then fill the device 10 with the desired medicine.

Figure 8:
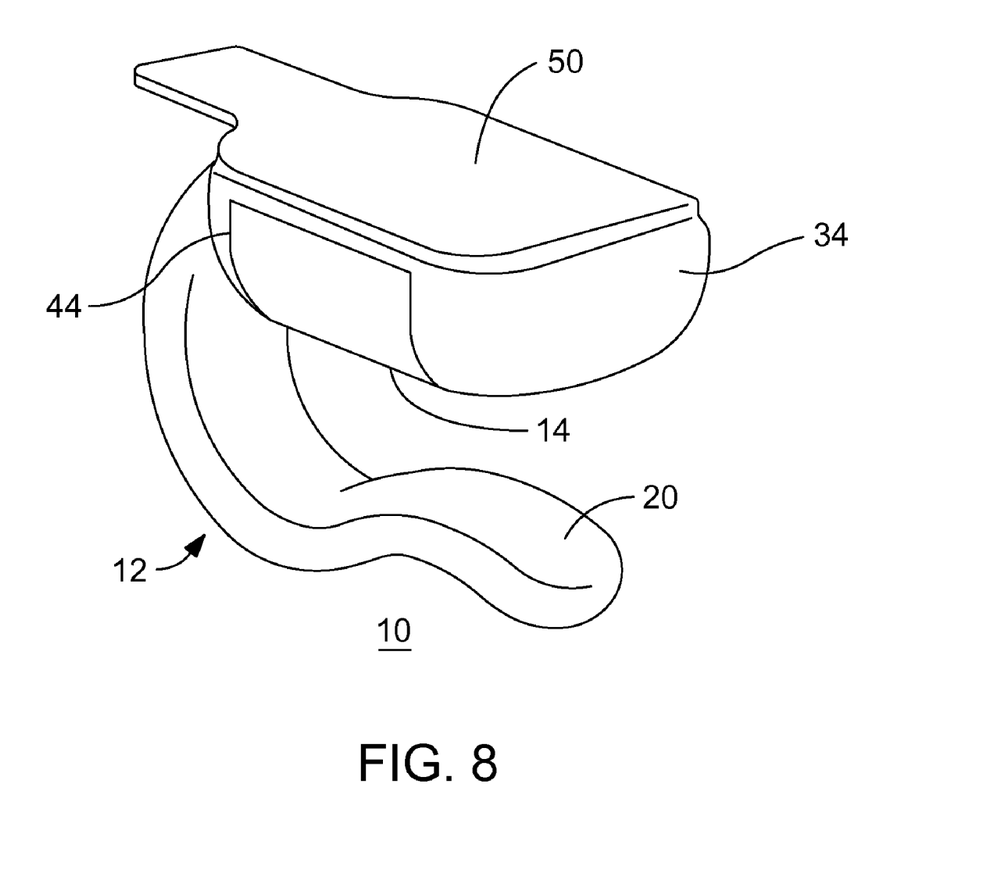
FIG. 8 is a perspective view of a medicinal delivery device according to another embodiment of the presently disclosed subject matter.

As illustrated in FIG. 8, a resilient pad 44 may be provided on the inner ala-engaging portion 14. The pad 44 may extend so as to cover the slot 42 defined in the housing 34. In this manner, the pad 44 provides comfort to the patient's skin, and also prevents flow-through of medicine through the slot 42, medicine which may otherwise contact the patient's skin and cause irritation thereto.

As also illustrated in FIG. 8, the device 10 may further include a selectively removable seal 50. The seal 50 extends from each respective end of the housing 34 and across the cover 36. In this manner, medicine cannot leak through the cover 36 until the seal 50 is removed. In combination with the resilient pad 44, the seal and pad 44 provide an air-tight and sun impermeable surface that will aid in maintaining the medicine until use on a patient. The seal 50 may have an adhesive, such as a pressure sensitive adhesive, applied on the device facing side of the seal 50 that adheres the seal 50 to the device 10. In one or more additional embodiments, the device 10 could be pre-packaged in a sealed container or wrapping such as vacuum packed plastic.

As illustrated throughout the Figures, the clip 12 may generally approximate a "U" in shape, while other arcuate and non-arcuate shapes may be properly embodied with the present invention. Additionally, the clip 12 may define an outwardly extending arcuate flange 30 on the first end 16. The flange 30 may be provided for providing a surface for removal of the device 10. In other words, the flange 30 is easily grasped or hooked by a patient or medical provider's hand or digit for sliding the device 10 away from the patient's nose 1. The clip 12 may be made from any suitable material, and in one or more embodiments, may be made of an acceptable medical grade plastic having sufficient flexibility and resiliency for being fitted to patients having different size noses and alas.

The device 10 is shown installed on the patient's nose 1 in FIG. 1. The device 10 is installed by being positioned proximal the patient's ala 3 and then further positioning the device 10 until the gap 24 receives the ala 3. The clip 12 may be bent outwardly so as to enlarge the gap 24 and then released so that the gap 24 returns to its initial size and the clip 12 is in engagement with the patient's ala 3. As illustrated in FIG. 1, the device 10 is installed on one nostril of the patient, but in appropriate circumstances may be installed on both nostrils of the patient.

Several aspects of the disclosed subject matter may be modified for appropriate applications of the device 10. For example, the diameter and other suitable dimensions of the clip 12 may be varied depending on the size of the patient's nose or other desired parameters. Additionally, vents 46 may have different sizes and shapes depending on the desired flow rate of medicine, the type of medicine being used, aesthetic qualities, or any other suitable factor.

The description and claims reference a patient, which as used in this application, is meant to refer to any person using the device 10. In many instances, the device 10 will be installed on a patient in a medical setting, such as at a hospital as an alternative to anesthesia treatment. Additionally, the device 10 may be used in other medical settings, such as with use for treating stress-related disorders or for use with treating post-surgical insomnia, and may be optionally used in conjunction with other medical devices or forms of treatment such as in combination with virtual reality hardware. The device 10 may also be suitable for at home use by a patient for use in medical or recreational application.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A medicinal delivery device comprising:
   a clip defining an ala inner surface-engaging portion about a first end thereof and an ala outer surface-engaging portion about a second end thereof in spaced-apart, generally facing arrangement relative to the first end to thereby define a gap therebetween for receiving a patient's ala;
   a medicine chamber carried about the first end of the clip for dispensing medicine into the patient's nasal cavity, the medicine chamber including a housing that defines a cavity therein;
   a cover configured for being at least partially received within the cavity and enclosing the chamber for storing medicine therein; and
   at least one upwardly facing vent defined in a portion of the cover that is received within the cavity of the medicine chamber for allowing flow-through of medicine into the patient's nasal cavity when the device is installed within the patient's nasal cavity.

2. The device according to claim 1, wherein the clip generally approximates a U-shape.

3. The device according to claim 1, wherein the clip defines an outwardly extending arcuate flange on the first end thereof for providing a surface for removal of the clip.

4. The device according to claim 1, wherein the cover defines a tab and the housing defines a slot for receiving the tab and selectively engaging the cover thereto.

5. The device according to claim 4, further including a resilient pad on the ala inner surface-engaging portion that extends so as to cover the slot, wherein the pad is for providing comfort to the patient's skin and for preventing flow-through of medicine through the slot.

6. The device according to claim 1, further including a selectively removable seal that extends across the cover and a surface of the housing for sealing the medicine therein.

7. The device according to claim 1, wherein the medicine is carried by an absorbent material.

8. The device according to claim 1, wherein the ala inner-surface engaging portion and the ala outer surface-engaging portion are in general aligned, opposing arrangement.

9. The device according to claim 1, wherein an outerfacing surface of the cover is generally aligned with an outermost surface of the chamber.

10. The device according to claim 1, wherein the housing defines a generally flat surface to which a medicament is applied.

11. A medicinal delivery device comprising:
    a generally arcuate clip having first and second ends, wherein the first end defines an ala inner surface-engaging portion and the second end defines an ala outer surface-engaging portion in spaced-apart and mutually facing and aligned arrangement relative to the ala inner surface-engaging portion to thereby form a gap therebetween for receiving a patient's ala;
    a medicine chamber carried about the first end and defining a cavity within a housing for containing a medicine, the housing defining a generally flat surface to which a medicine is applied; and
    a cover in selective engagement with the housing for enclosing the medicine and further defining at least one upwardly facing vent for allowing flow-through of medicine into the patient's nasal cavity when the device is installed within the nasal cavity of a patient and having at least one tab that is configured for engaging within the housing to thereby secure the cover to the chamber, wherein the cover is at least partially received within the housing and an outerfacing surface of the cover is generally aligned with an outermost surface of the chamber, and further wherein the at least one upwardly facing vent is defined in a portion of the cover that is received within the cavity of the medicine chamber.

12. The device according to claim 11, wherein the clip defines an outwardly extending arcuate flange on the first end thereof for providing a surface for removal of the clip.

13. The device according to claim 11, further including a selectively removable seal that extends across the cover and the housing for sealing the medicine therein.

14. The device according to claim 11, wherein the medicine is carried on an absorbent material.

15. The device according to claim 11, further including a resilient pad on the ala inner surface-engaging portion for providing comfort to the patient's skin.

* * * * *